United States Patent [19]

Kugai

[11] Patent Number: 5,990,678
[45] Date of Patent: *Nov. 23, 1999

[54] NON-DESTRUCTIVE TESTING EQUIPMENT HAVING SQUID TYPE MAGNETIC SENSOR

[75] Inventor: Hirokazu Kugai, Hyogo, Japan

[73] Assignee: Sumitomo Electric Industries, Ltd., Osaka, Japan

[ * ] Notice: This patent is subject to a terminal disclaimer.

[21] Appl. No.: 08/653,328

[22] Filed: May 24, 1996

Related U.S. Application Data

[63] Continuation of application No. 08/273,947, Jul. 12, 1994, Pat. No. 5,589,772.

[30] Foreign Application Priority Data

Jul. 12, 1993 [JP] Japan ................................. 5-195125
Dec. 27, 1993 [JP] Japan ................................. 5-348837

[51] Int. Cl.$^6$ .................. G01R 33/12; G01R 33/035; G01N 27/72
[52] U.S. Cl. ..................... 324/240; 324/225; 324/262; 505/846
[58] Field of Search ................... 324/248, 202, 324/219–221, 224–228, 239–244, 260–262; 505/845, 846, 842, 843; 327/527

[56] References Cited

U.S. PATENT DOCUMENTS

| | | | |
|---|---|---|---|
| 4,258,319 | 3/1981 | Shimada et al. | 324/226 |
| 4,613,816 | 9/1986 | Zeamer | 324/248 |
| 4,855,678 | 8/1989 | Kreiskorte | 324/225 |
| 5,004,724 | 4/1991 | De | 324/248 |
| 5,059,903 | 10/1991 | Otaka et al. | 324/223 |
| 5,134,368 | 7/1992 | Otaka et al. | 324/248 |
| 5,293,119 | 3/1994 | Podney | 324/242 |
| 5,331,278 | 7/1994 | Evanson et al. | 324/232 |
| 5,430,376 | 7/1995 | Viertl | 324/227 |

*Primary Examiner*—Walter E. Snow
*Attorney, Agent, or Firm*—Kerkam, Stowell, Kondracki & Clarke, P.C.; John C. Kerins

[57] ABSTRACT

A non-destructive testing equipment comprises a magnetic field generator for generating a uniform magnetic field, and a magnetic sensor accommodated in a thermal insulation container and filled with a liquid nitrogen. The thermal insulation container is located within a magnetic shield container having an opening. The magnetic sensor includes a SQUID that is a magnetic sensor having very high sensitivity. The magnetic sensor can detect, through the opening, an appreciable variation of the magnetic field that is caused by small impurities or minor defects contained in the object to be tested.

5 Claims, 7 Drawing Sheets

NON-DESTRUCTIVE TESTING EQUIPMENT HAVING SQUID TYPE MAGNETIC SENSOR

This application is a continuation of application Ser. No. 08/273,947, filed Jul. 12, 1994 now abandoned U.S. Pat. No. 5,589,772.

BACKGROUND OF THE INVENTION

1. Field of the Invention

The present invention relates to a non-destructive testing equipment, and more specifically, to a new portable magnetic testing equipment which can detect impurities or defects contained in an object to be tested, with high sensitivity.

2. Description of Related Art

A slight defect in a body of aircraft or spacecrafts and satellites will often results in a serious accident. Therefore, a periodical check and maintenance are severely performed for the body of these vehicles. However, since a so-called destructive testing cannot be performed for these bodies, the checkings being currently performed are limited to a checking by worker's eyes and an acoustic testing, so that a satisfactory checking precision and reliability cannot be obtained, and working efficiency of the checking operation is low.

In addition, in laid power transmission cables and laid signal transmission cables, it is possible to inspect a surface of these cables by human's eyes, and to evaluate the condition of conductors included in these cables on the basis of quality of transmission signals. However, there has not yet been proposed a method capable of inspecting an internal condition of insulators included in the cables and of testing tensile strength members themselves included in the cables. Similarly, it is very difficult to inspect an internal condition of structural wire-cables after assembled.

As mentioned above, in various technical fields, there are a large demand for a method or equipment for precisely detecting extremely small impurities or slight defects included in the materials having an extremely large length or a large area. However, such a method or equipment have not yet been proposed.

SUMMARY OF THE INVENTION

It is an object of the present invention to provide a non-destructive testing equipment which has overcome the above mentioned defect of the conventional ones.

Another object of the present invention is to provide a non-destructive testing equipment which can precisely and efficiently inspect a large scaled member or structure.

Still another object of the present invention is to provide a non-destructive testing equipment which can efficiently inspect an object to be tested, such as a laid signal transmission cable, a laid power transmission cable, or an assembled structural member, all of which cannot be easily moved, detached or disassembled.

The above and other objects of the present invention are achieved in accordance with the present invention by a non-destructive testing equipment comprising a magnetic shield container defining a magnetically stable inspection zone and having a magnetically transparent opening facing the inspection zone; a magnetic field generator attached to the magnetic shield container, for generating a stable magnetic field in the inspection zone; a magnetic sensor located in the magnetic shield container and including at least one SQUID (Superconducting Quantum Interference Device), for detecting, through the opening, the magnetic field in the inspection zone; and means provided to the magnetic shield container, for cooling the magnetic sensor, the testing equipment being so configured so as to move in relation to and along an objected to be tested, while maintaining a positional relation between the magnetic sensor and the objected to be tested.

With this arrangement, a minute variation of the magnetic field which is caused by impurities or defects contained in the object to be tested, can be detected by a super high sensitive SQUID type magnetic sensor. In addition, it is possible to inspect an outdoor stationary object to be tested, such as a large scaled structure and a laid cable.

In brief, a fixed magnetic field is generated by the magnetic field generator in the inspection zone which is prevented from influence of the environment magnetic field by the magnetic shield container. If an object to be tested is located in the inspection zone having the fixed magnetic field, some change occurs in the magnetic field in accordance with a magnetic susceptibility or magnetization of the object to be tested. However, the object to be tested contains impurities or defects, the magnetic field shows a unique change which is caused by existence of the impurities or the defects. This unique change of the magnetic field can be sensed by the super high sensitive SQUID magnetic sensor, even if it is very slight. Thus, the object to be tested can be quickly and precisely inspected non-destructively.

As mentioned above, the above mentioned testing equipment comprises the magnetic shield container for forming the inspection zone substantially shielded from the environment magnetic field, and the magnetic field generator for generating the stable magnetic field in the inspection zone. For this purpose, the magnetic shield container can be formed of for example permalloy.

The non-destructive testing equipment in accordance with the present invention additionally comprises a cooling means for cooling the SQUID used in the magnetic sensor. Since the SQUID is composed of a superconducting loop including a weak link, when the non-destructive testing equipment is put in operation, it is necessary to cool the magnetic sensor down to a temperature not higher than a superconducting critical temperature. For this purpose, one embodiment of the non-destructive testing equipment in accordance with the present invention includes a thermal insulation container which is filled with a cooling medium and in which the magnetic sensor is located so that the magnetic sensor is immersed in the cooling medium when the non-destructive testing equipment is in operation.

In an embodiment of the non-destructive testing equipment in accordance with the present invention, the SQUID is preferably formed of an oxide superconducting thin film. In general, oxide superconducting materials become a superconducting state at a temperature obtained by an inexpensive liquid nitrogen. Accordingly, by locating the SQUID in the thermal insulation container and filling the thermal insulation container with the liquid nitrogen, it is possible to relatively easily and inexpensively construct a portable non-destructive testing equipment. In addition, in place of using the liquid nitrogen, it is possible to cool the magnetic sensor by use of a small scaled cooling machine capable of cooling to a temperature not higher than a superconducting critical temperature.

Furthermore, in an actual operation of this non-destructive testing equipment, it is preferable to provide a temperature sensor which monitors at least the temperature in proximity of the SQUID and alarms when the temperature rises abnormally. The reason for this is that a superconducting circuit including the SQUID normally operates only at the temperature not higher than a superconducting critical temperature. If the superconducting condition is broken, not only the superconducting circuit does not normally operate, but also the superconducting circuit may be broken in extreme cases.

Further, in order to ensure that the whole of the non-destructive testing equipment is portable, the magnetic field generator can be preferably constituted of a permanent magnet unit which needs no additional resource such as an electric power supply. Alternatively, the magnetic field generator can be formed of a solenoid configured to be able to be easily connected to an external electric power supply.

The above and other objects, features and advantages of the present invention will be apparent from the following description of preferred embodiments of this invention with reference to the accompanying drawings.

DESCRIPTION OF PREFERRED EMBODIMENTS

Figure 1:
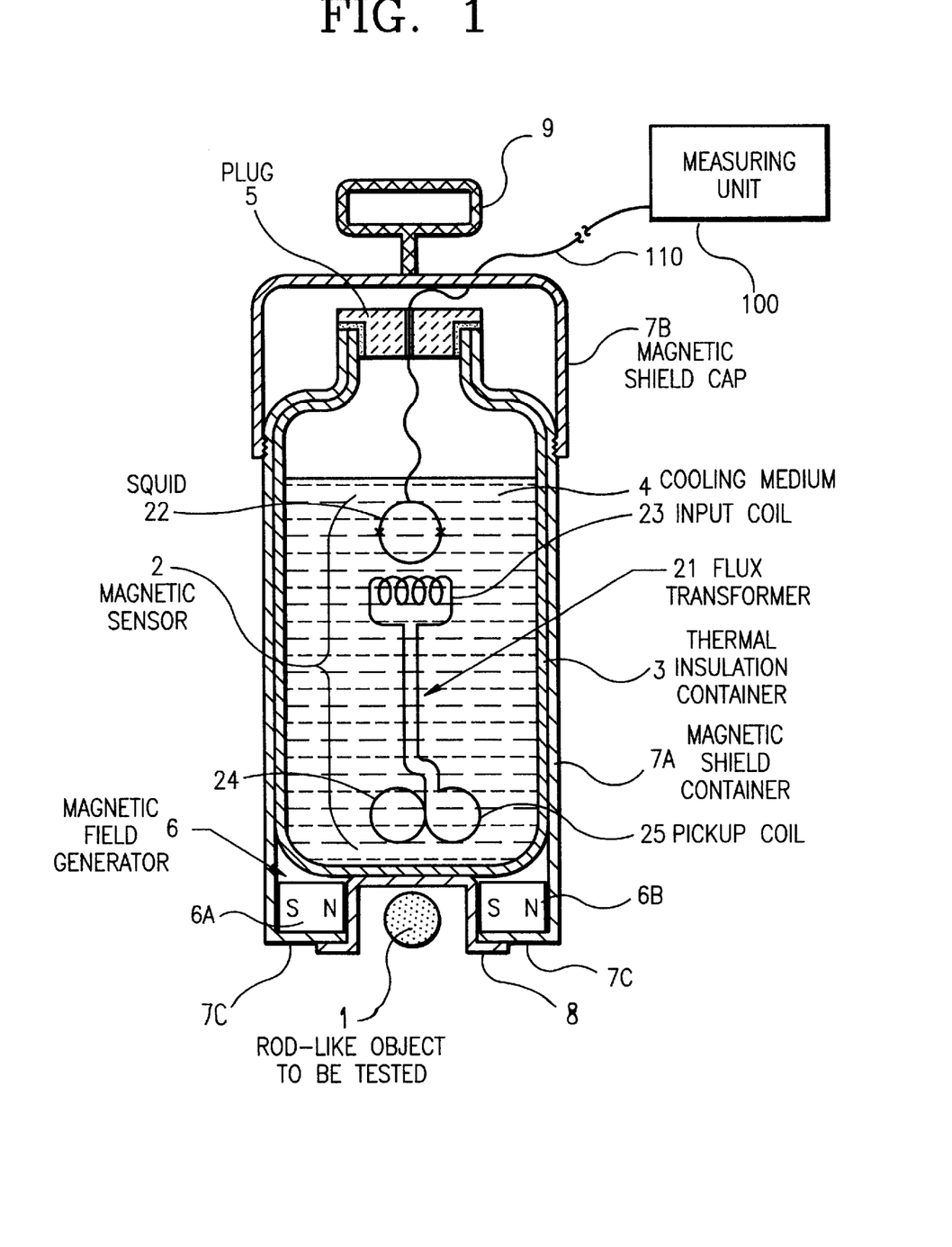
FIG. 1 is a diagrammatic sectional view showing a first embodiment of the non-destructive testing equipment in accordance with the present invention.

Referring to FIG. 1, there is shown a diagrammatic sectional view showing a first embodiment of the non-destructive testing equipment in accordance with the present invention.

The shown non-destructive testing equipment is configured to inspect an object 1 to be tested in the form of a continuous rod or wire. A magnetic sensor 2 is located in a non-magnetic thermal insulation container 3 filled with a cooling medium 4 such as a liquid nitrogen. An upper end of the container 3 can be hermetically closed with a thermal insulation plug 5.

A magnetic field generator 6 is located on an outer surface of a lower closed bottom of the container 3. This magnetic field generator 6 is constituted of for example a pair of permanent magnet units 6A and 6B, which are separated from each other so as to form a space therebetween in which the rod-like object 1 to be tested can be positioned, so that a magnetic field from one permanent magnet unit 6A to the other permanent magnet unit 6B passes through the rod-like object 1 to be tested, perpendicularly to a lengthwise direction of the rod-like object 1 to be tested.

The thermal insulation container 3 and the magnetic field generator 6 are located or fitted in a magnetic shield container 7A, which is formed of for example permalloy. An upper portion of the magnetic shield container 7A is covered or fitted with a magnetic shield cap 7B, which is also formed of for example permalloy. A lower end of the magnetic shield container 7A has an inward flange 7C so configured to support the pair of permanent magnet units 6A and 6B between the inward flange 7C and the bottom surface of the thermal insulation container 3.

A magnetically transparent opening or window defined by the inward flange 7C is fitted with a non-magnetic concave protection member 8, which also functions as a spacer for separating the permanent magnet units 6A and 6B from each other so as to ensure the above mentioned space therebetween in which the rod-like object 1 to be tested can be positioned. This protection member 8 is preferably formed of a material having a highly wear resistant property and a very low coefficient of surface friction. For example, the protection member 8 can be formed of various kinds of ceramics material or a fluoroplastics or fluororesin.

As shown in FIG. 1, the magnetic sensor 2 comprises a SQUID 22 and a flux transformer 21, both of which are immersed in the cooling medium 4. However, the magnetic sensor 2 can be constituted of only the SQUID 22.

For example, the flux transformer 21 has a pickup coil and an input coil 23 interconnected to form a closed loop. The pickup coil is formed of at least a pair of coils 24 and 25 having their winding directions opposite to each other, so that the whole of the magnetic sensor is in the form of a so-called "gradiometer".

Since the coils 24 and 25 are wound in directions opposite to each other, respective currents induced in the coils 24 and 25 by a spatially uniform magnetic field are opposite in direction to each other, and therefore are cancelled. An environment magnetic field which might influence the coils 24 and 25 through the magnetically transparent opening closed with the non-magnetic protection member 8, can be regarded as being spatially uniform in a small area occupied by these the coils 24 and 25. Therefore, not only the environment magnetic field is shielded by the magnetic shield container 7A and the magnetic shield cap 7B, but also influence of the environment magnetic field to the magnetic sensor, which should be very slight because of the magnetic shield, can be cancelled in the gradiometer type magnetic sensor.

On the other hand, a variation of the magnetic field caused by the impurities or defects included in the object to be tested, is extremely localized, and therefore, a magnetic gradient occurs between the coils 24 and 25. Namely, the variation of the magnetic field caused by the impurities or defects can be detected by the gradiometer type magnetic sensor. In this connection, in order to easily and surely detect the magnetic gradient between the coils 24 and 25 caused by the impurities or defects, it is preferred to locate the coils 24 and 25 in such a manner that a distance between the object to be tested and the coil 24 is substantially different from a distance between the object to be tested and the coil 25, as diagrammatically illustrated in FIG. 1.

The flux transformer 21 is magnetically coupled to the SQUID 22, in particular at its input coil 23. The SQUID 22 is connected to a measuring unit 100 located at an external of the non-destructive testing equipment, through a cable 110 extending through the plug 5 and through. the cap 7B. The SQUID 22 is formed of for example a high temperature oxide superconducting material.

A handle 9 is mounted on a top of the cap 7B, so that an operator can transport the non-destructive testing equipment by griping and suspending the handle 9 by his hand. If the non-destructive testing equipment is suspended by griping the handle 9 by the operator's hand, it is possible to maintain the non-destructive testing equipment in a standing. position in which the plug 5 is at the top and the closed end of the container 3 is at the bottom. Namely, the magnetic sensor 2, particularly the SQUID 22 is prevented from being exposed from the cooling medium 4. If the SQUID 22 were exposed from the cooling medium 4, the superconducting state of the SQUID and the associated superconducting circuit would be broken so that the magnetic sensor would not properly operate.

Principle of operation of the testing equipment shown in FIG. 1 will be now described with reference to FIGS. 2A through 2C.

Figure 2A:
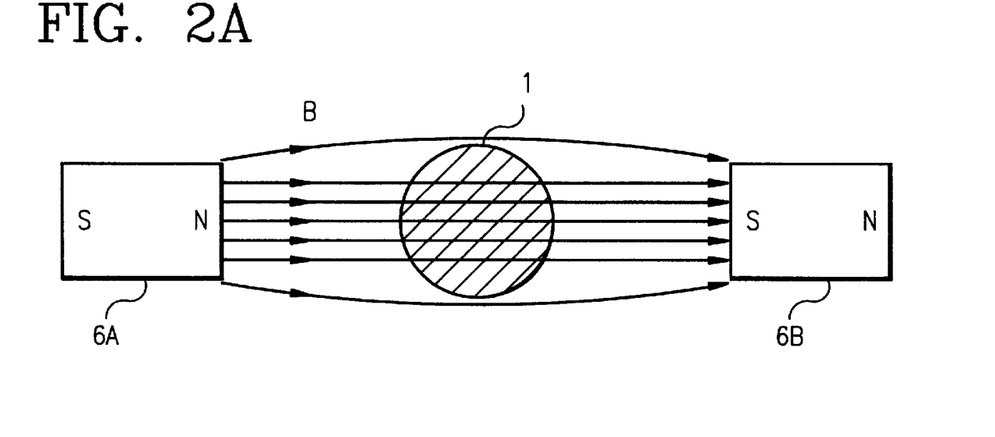
FIGS. 2A, 2B and 2C are magnetic field diagrams illustrating a defect/impurity inspection theory of the non-destructive testing equipment in accordance with the present invention.

As shown in the FIG. 2A, assume that a uniform magnetic field B is generated between the permanent magnet units 6A and 6B. When the object 1 to be tested is located within the uniform magnetic field B, the magnetic field changes in accordance with a magnetic susceptibility or magnetization of the object 1 to be tested, but becomes stable if the object 1 to be tested has neither an impurity nor a defect.

Figure 2B:
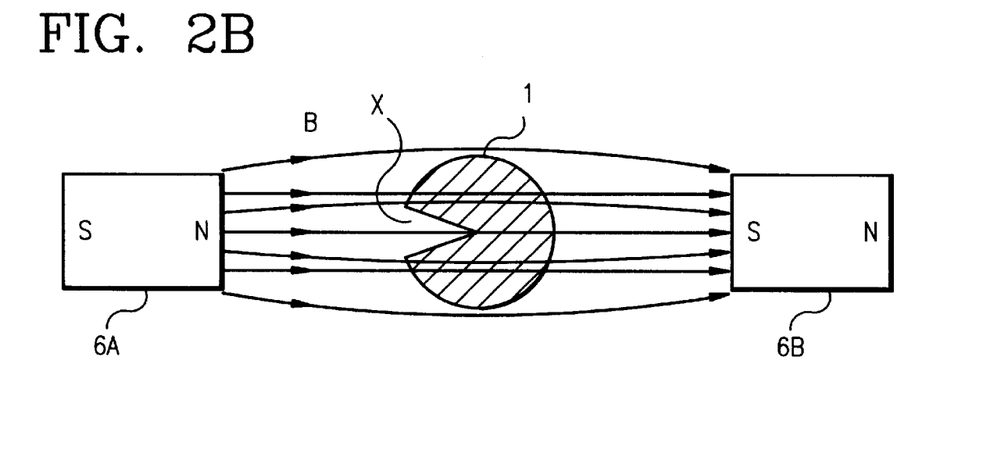
Figure 2C:
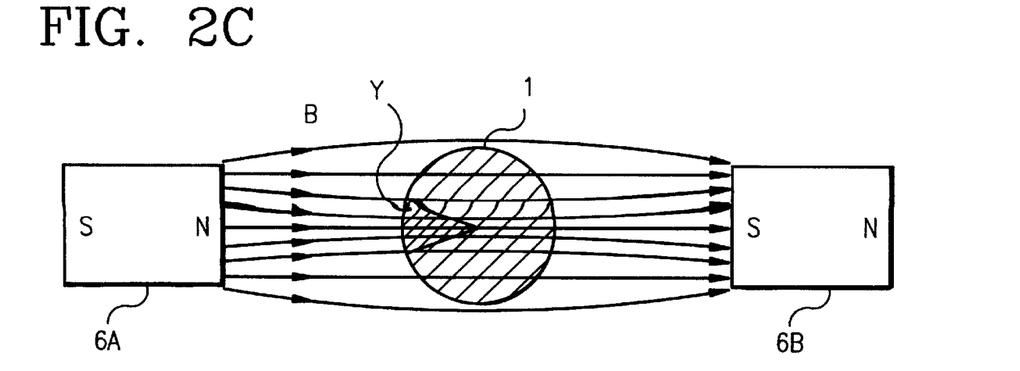

When the object 1 to be tested contains a defect X as shown in the FIG. 2B or an impurity Y as shown in the FIG. 2C, the magnetic field B shows an appreciable change in accordance with the defect X or a magnetic susceptibility or magnetization of the impurity Y. The appreciable change of the magnetic field B is detected by the magnetic sensor, which outputs the result of the detection in the form of a voltage signal.

Figure 3:
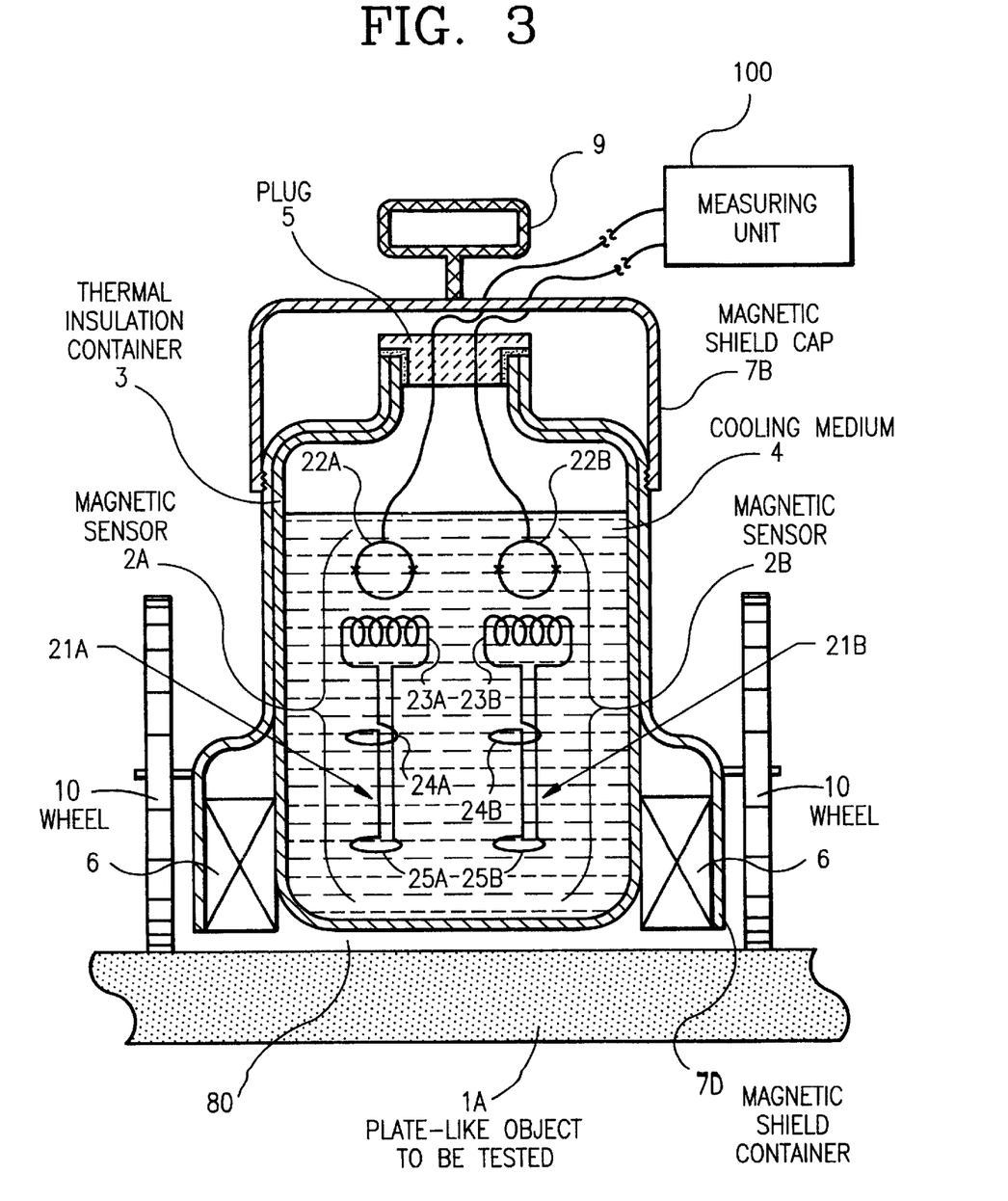
FIG. 3 is a diagrammatic sectional view of another embodiment of the non-destructive testing equipment in accordance with the present invention.

Referring to FIG. 3, there is shown another embodiment of the testing equipment in accordance with the present invention, which is configured to inspect an object 1A to be tested in the form of a wide plate-like material in a large scaled structure such as a body of aircraft. FIG. 3 is a sectional view taken along in a plane perpendicular to the travelling direction of the testing equipment. In addition, in FIG. 3, elements similar or corresponding in function or in construction to those shown in FIG. 1 are given the same Reference Numerals, and explanation thereof will be omitted.

The thermal insulation container 3 is widened in comparison with that of the first embodiment shown in FIG. 1, and a plurality of magnetic sensors 2A and 2B are located in the thermal insulation container 3, instead of a single magnetic sensor 2 in the first embodiment shown in FIG. 1. Each of the magnetic sensors 2A and 2B includes a SQUID 22A or 22B and a flux transformer 21A or 21B, both of which are immersed in the cooling medium 4. Each of the flux transformers 21A and 21B has a pickup coil and an input coil 23A or 23B interconnected to form a closed loop. The pickup coil is formed of a pair of coils 24A and 25A or 24B and 25B having their winding directions opposite to each other, so that the whole of each magnetic sensor is in the form of a so-called "gradiometer".

Furthermore, as the magnetic field generator, a solenoid 6 is mounted to surround a lower portion of the thermal insulation container 3. A magnetic shield container 7D has an expanded or flared open lower end so that the solenoid 6 is sandwiched and supported between the outer side surface of the lower portion of the thermal insulation container 3 and the expanded lower portion of the magnetic shield container 7D.

Furthermore, a plurality of wheels 10 are rotatably mounted at a side of the magnetic shield container 7D. These wheels 10 make it possible for the non-destructive testing equipment to smoothly move on the plate-like object 1A to be tested, while maintaining a spacing 80 between the bottom surface of the non-destructive testing equipment and the plate-like object 1A to be tested, namely a distance between the magnetic sensors 2A and 2B and the plate-like object 1A to be tested.

In FIG. 3, only two wheels 10 are shown. However, in order to precisely maintain the distance between the magnetic sensors 2A and 2B and the plate-like object 1A to be tested at a constant value, three or more wheels are preferably mounted. Furthermore, the non-destructive testing equipment can include a driving motor coupled to drive the wheels 10, so that the non-destructive testing equipment is made to a self-propelled type. This self-propelled non-destructive testing equipment would make easy an internal inspect of a pipe in laid pipe lines, and would also make it possible to perform an inspection at a location such as in nuclear installations to which a human being is very difficult to access.

Figure 4A:
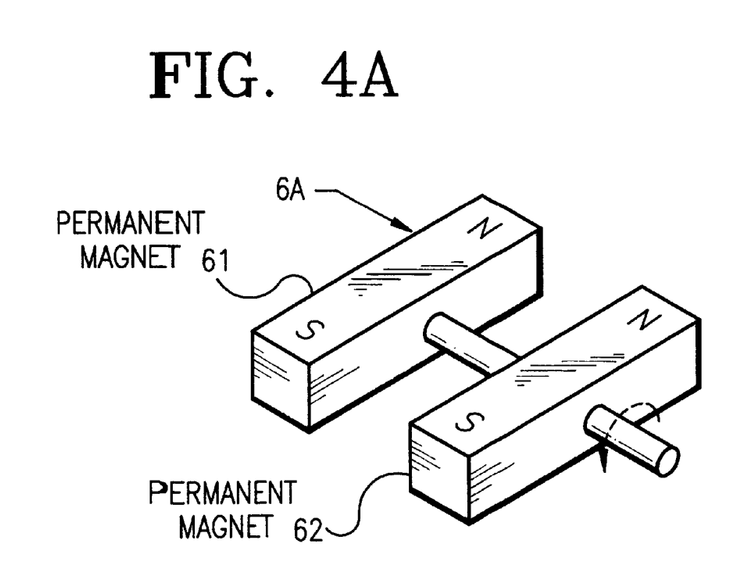
FIGS. 4A and 4B are diagrammatic perspective views, in a first operational condition, of a specific example of the magnetic field generator used in the non-destructive testing device in accordance with the present invention, illustrating permanent magnet units 6A and 6B, respectively.
Figure 4B:
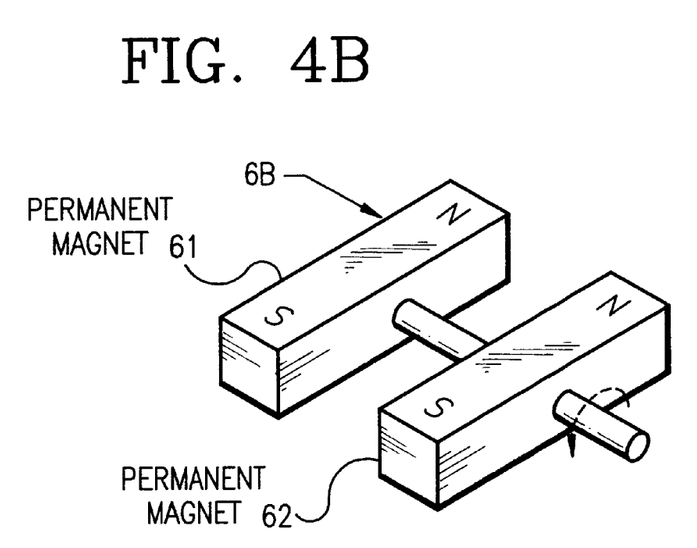
Figure 4C:
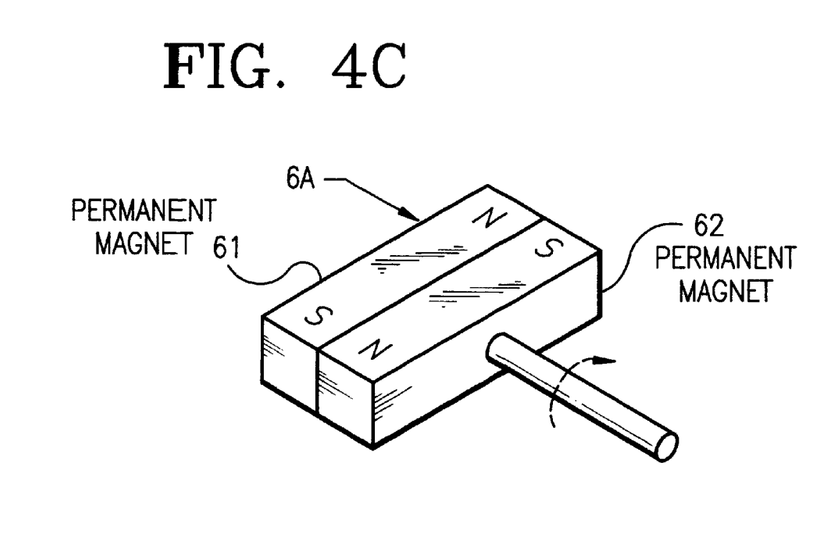
FIGS. 4C and 4D are diagrammatic perspective views, in a second operational condition, of the specific example of the magnetic field generator illustrated in FIGS. 4A and 4B.
Figure 4D:
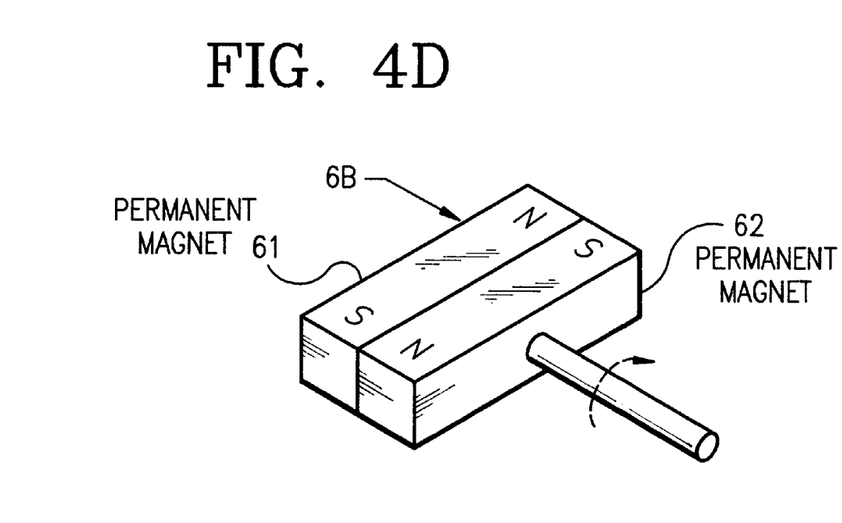

Referring to FIGS. 4A and 4B, one preferred example of the magnetic field generator is illustrated in two different conditions.

As shown in FIG. 4A, each of the permanent magnet units 6A and 6B includes a pair of permanent magnets 61 and 62, one of the permanent magnets 61 being stationary, and the other permanent magnet 62 being rotatable as indicated by a dotted line.

When the portable testing equipment is put in operation, the permanent magnets 61 and 62 are located in parallel to each other and in the same polarity direction as shown in FIG. 4A, so that the permanent magnets 61 and 62 are magnetically strongly repelled and separated from each other. In this case, a substantial magnetic field is generated in the outside of the permanent magnets 61 and 62, so that a magnetic field extending from the permanent magnet unit 6A to the permanent magnet unit 6B is created.

If the testing is completed, the permanent magnet 62 is rotated 180 degrees so that the permanent magnets 61 and 62 are located in parallel to each other but opposed to each other in polarity as shown in FIG. 4B. In this situation, the permanent magnets 61 and 62 are magnetically strongly bonded to each other as shown in FIG. 4B, and, the magnetic flux are looped in the two permanent magnets 61 and 62 magnetically bonded to each other. In other words, no substantial magnetic field is generated in the outside of the magnetically bonded permanent magnets 61 and 62.

Figure 5A:
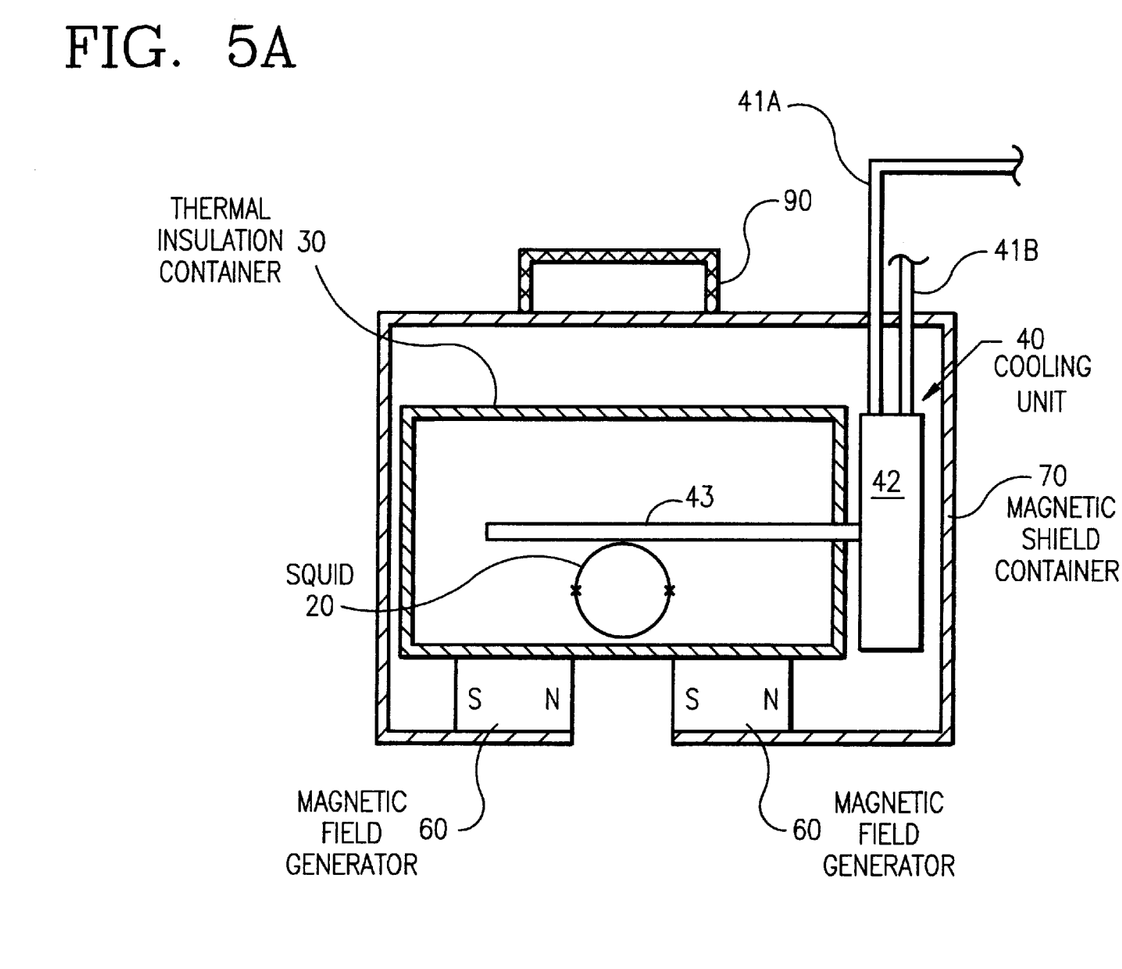
FIGS. 5A and 5B are diagrammatic sectional views of third and fourth embodiments of the non-destructive testing equipment in accordance with the present invention.

Referring to FIG. 5A, there is shown a diagrammatic sectional view of a third embodiment of the non-destructive testing equipment in accordance with the present invention.

Differently from the first and second embodiments, the third embodiment includes a cooling unit 40 and is still portable as a whole.

The third embodiment includes a magnetic shield container 70 in the form of a box, which has a handle 90 mounted on an upper surface thereof and an opening formed at a bottom thereof. A pair of magnetic field generators 60 are located on a periphery of the opening. A non-magnetic thermal insulation container 30 is located on the pair of magnetic field generators 60 and is completely housed in the magnetic shield container 70. Within the thermal insulation container 30, a SQUID 20 is located.

In addition, a small-sized Joule-Thomson type cooling machine 42 is located within the magnetic shield container 70 adjacent to the thermal insulation container 30. This Joule-Thomson type cooling machine 42 has a cooling table or bar 43 extending into the thermal insulation container 30 and passing in proximity of the SQUID 20. The Joule-Thomson type cooling machine 42 can be coupled through a pipe 41A to an external cooling medium tank (not shown) such as a high pressure nitrogen gas cylinder. The cooling machine 42 is also coupled to an exhausting pipe 41B. Thus, the Joule-Thomson type cooling machine 42 can cool down and maintain the SQUID 20 at a temperature not higher than a superconducting critical temperature.

It will be apparent to persons skilled in the art that this third embodiment of the non-destructive testing equipment is the same in inspection operation as the first and second embodiments, and therefore, explanation of the inspection operation will be omitted.

Thus, this non-destructive testing equipment can be used in the outdoor for a long period of time, for example, for inspecting a laid cable or others, since the SQUID can be maintained in a superconducting state for a sufficiently long period of time by action of the built-in cooling unit 40.

Figure 5B:
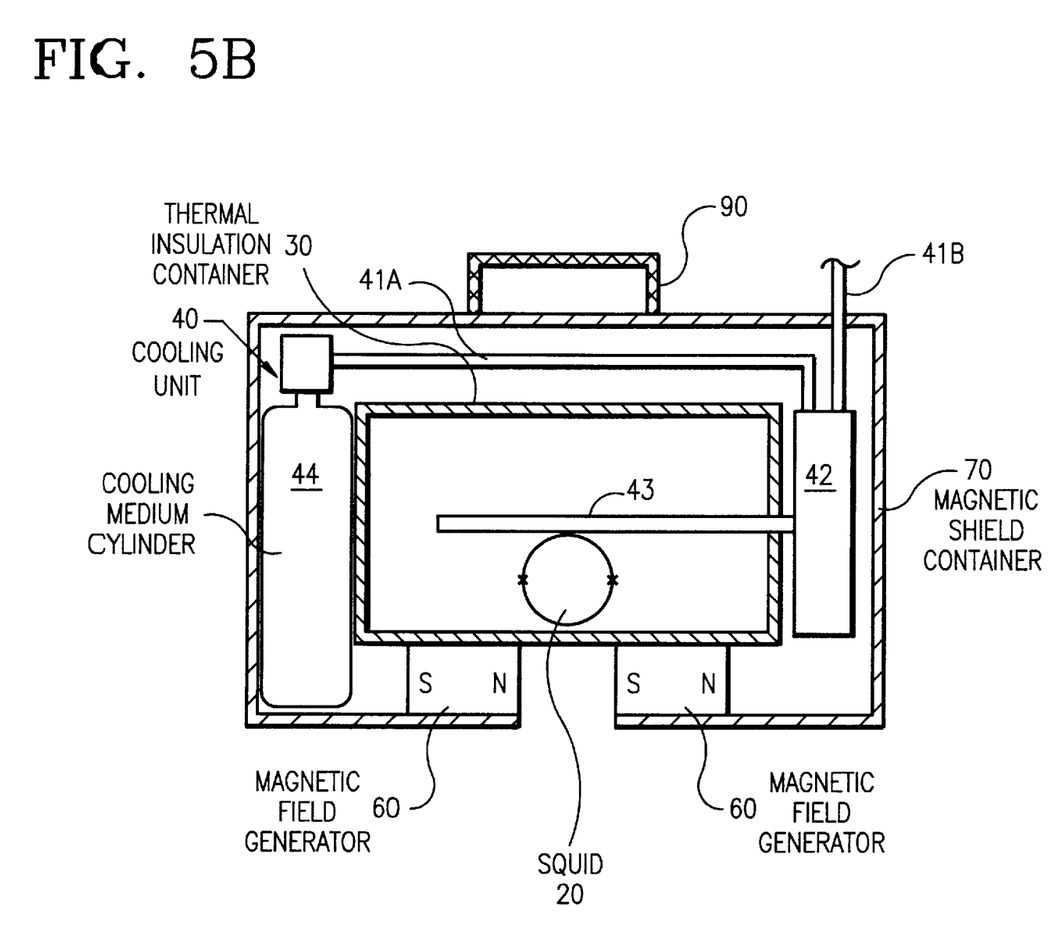

Referring to FIG. 5B, there is shown a fourth embodiment which is a modification of the third embodiment. In FIG. 5B, therefore, elements corresponding to those shown in FIG. 5A are given the same Reference Numerals, and explanation thereof will be omitted. This fourth embodiment includes a cooling medium cylinder 44 located within the magnetic shield container 70 adjacent to the thermal insulation container 30 and coupled to the cooling machine 42 within the magnetic shield container 70.

Since this fourth embodiment contains the necessary cooling medium supply therein, it is possible to use the non-destructive testing equipment independently of a cooling medium supply, and therefore, application of the non-destructive testing equipment can be further extended As will be apparent from the above, the third and fourth embodiments can assume an arbitrary attitude or inclination, differently from the first and second embodiment. Therefore, the third and fourth embodiments can be advantageously used for the purpose of inspecting a large-scaled structure such as a body of aircraft.

Accordingly, the non-destructive testing equipment in accordance with the present invention can quickly and precisely detect an extremely small defects or impurities, and also has a portability. In addition, if a plurality of magnetic sensors are incorporated, it is also possible to detect not only existence of defects or impurities but also positions of defects or impurities and distribution of defects or impurities.

Furthermore, in the case that the cooling unit is incorporated in the non-destructive testing equipment, it is possible to freely use the non-destructive testing equipment in the outdoor. Accordingly, the non-destructive testing equipment can be advantageously used for inspecting the laid and fixed cables, a body and frames of large-scaled vehicles such as ships and aircraft, and a large scaled stationary structure such as iron bridges and other iron structures.

The present invention has thus been shown and described with reference to the specific embodiments. However, it should be noted that the present invention is in no way limited the details of the illustrated structures but converts and modifications may be made within the scope of the appended claims.

What is claimed is:

1. A non-destructive testing device comprising:

a magnetic shield container defining a magnetically stable inspection zone outside of said container where an object to be tested is to be positioned for testing and said magnetic shield container having a magnetically transparent opening adjacent said inspection zone;

a magnetic field generator attached to said magnetic shield container, for generating a stable magnetic field in said inspection zone;

a magnetic sensor located in said magnetic shield container and having at least one SQUID, for detecting, through said opening, the magnetic field in said inspection zone;

means provided to said magnetic shield container, for cooling said magnetic sensor, means for allowing the testing device to move in relation to and along an object to be tested, and means for maintaining a constant spacing between the object to be tested and a surface of said device positioned adjacent to said object when said object is undergoing testing, and means for outputting a signal when an appreciable change in said magnetic field is detected by said magnetic sensor as said sensor is moved relative to an object to be tested.

2. A testing device according to claim 1 wherein said cooling means includes a thermal insulation container accommodating said magnetic sensor therein and filled with a cooling medium for cooling said magnetic sensor to a temperature not higher than a superconducting critical temperature.

3. A testing device according to claim 1 further including a non-magnetic spacer provided on said magnetic shield container at a side of said opening, for maintaining a distance between said magnetic sensor and the object to be tested.

4. A testing device according to claim 1 further including a plurality of non-magnetic wheels provided on said magnetic shield container at a side of said opening, for rolling on a surface of the object to be tested, while maintaining a distance between said magnetic sensor and the object to be tested.

5. A testing device according to claim 1 wherein said magnetic sensor comprises a flux transformer magnetically coupled to said SQUID, and said flux transformer includes at least a pair of pickup coils wound in directions opposite to each other, so that said magnetic sensor constitutes a gradiometer.

* * * * *